(12) United States Patent
Peters (10) Patent No.: US 9,504,817 B2
(45) Date of Patent: Nov. 29, 2016

(54) DUAL-VALVE CONTRAST FLUID DELIVERY SYSTEM

(76) Inventor: Jean-Pierre Peters, Hasselt (BE)

(*) Notice: Subject to any disclaimer, the term of this patent is extended or adjusted under 35 U.S.C. 154(b) by 0 days.

(21) Appl. No.: 14/232,777

(22) PCT Filed: Jul. 15, 2011

(86) PCT No.: PCT/EP2011/062179
§ 371 (c)(1),
(2), (4) Date: Feb. 4, 2014

(87) PCT Pub. No.: WO2013/010572
PCT Pub. Date: Jan. 24, 2013

(65) Prior Publication Data
US 2014/0163364 A1   Jun. 12, 2014

(51) Int. Cl.
A61M 39/24 (2006.01)
A61M 39/10 (2006.01)
A61M 39/26 (2006.01)
A61M 39/28 (2006.01)
A61M 5/00 (2006.01)

(52) U.S. Cl.
CPC .......... *A61M 39/24* (2013.01); *A61M 39/1011* (2013.01); *A61M 39/26* (2013.01); *A61M 39/288* (2013.01); *A61M 5/007* (2013.01); *A61M 2039/1033* (2013.01)

(58) Field of Classification Search
CPC ........... A61M 5/168; A61M 39/1011; A61M 39/26; A61M 2039/1033
See application file for complete search history.

(56) References Cited

U.S. PATENT DOCUMENTS

| 5,569,208 A | 10/1996 | Woelpper et al. |
| 5,575,779 A | 11/1996 | Barry |
| 8,231,584 B2 * | 7/2012 | Peters ........................ 604/257 |
| 2002/0123737 A1 | 9/2002 | Hart et al. |

FOREIGN PATENT DOCUMENTS

| DE | 10 2008 036 728 A1 | 2/2010 |
| EP | 1 726 328 A1 | 11/2006 |
| WO | 2011/066865 A1 | 6/2011 |

OTHER PUBLICATIONS

International Search Report for PCT/EP2011/062179 dated Jul. 2, 2012.

* cited by examiner

*Primary Examiner* — Imani Hayman
*Assistant Examiner* — James D Ponton
(74) *Attorney, Agent, or Firm* — Sughrue Mion, PLLC (57) ABSTRACT

A disposable set (5) for establishing a fluid connection between a fluid dispensing unit (17) and a dosing device adapted to dispense the fluid into a patients' vein, the disposable set comprising a length of a tubing (15) for establishing a fluid connection from the fluid dispensing unit towards and into the dosing device, wherein the tubing (15) comprises a first (1) and a second (10) tubing part, and a releasable connection (11,12), wherein the first tubing part (1) comprises two or more one-way valves (3, 24) which are provided to prevent a backflow from the patient in the direction of the fluid dispensing unit (17) in the closed position of the releasable connection.

13 Claims, 2 Drawing Sheets

DUAL-VALVE CONTRAST FLUID DELIVERY SYSTEM

CROSS REFERENCE TO RELATED APPLICATIONS

This application is a National Stage of International Application No. PCT/EP2011/062179 filed Jul. 15, 2011, the contents of which are incorporated herein by reference in their entirety.

INTRODUCTION

The present invention relates to a disposable set for establishing a fluid connection between a fluid dispensing unit and a dosing device adapted to dispense the fluid into a patients' vein, the disposable set comprising a length of a tubing for establishing a fluid connection from the fluid dispensing unit towards and into the dosing device, according to the preamble of the first claim.

Contrast medium dispensing systems are well known in the art. The known fluid dispensing systems usually comprise a spike at one end for engaging the reservoir containing the contrast medium, and on the other end a mechanism with a luer connector for coupling the container to one port of a manifold. Another port of the manifold is coupled to a syringe adapted to administer the fluid into the patient's vein. To reduce waste, many contrast medium dispensing systems include a reservoir between the spike and the luer connector to temporarily hold a quantity of contrast medium.

Contrast medium dispensing systems are widely used for (optionally robotic) delivery of contrast media during enhanced imaging procedures with different modalities such as, but not limited to computed tomography (CT), magnetic resonance imaging (MRI), PET scanning and angiography. However, accidental patient cross contaminations with microbial flora (e.g., coagulase-negative staphylococci) and blood borne pathogenic microorganisms (viruses, bacteria, parasites, etc) associated with infectious diseases such as malaria, acquired immune deficiency syndrome, hepatitis C, and hepatitis B have been reported. Potential outbreak of proteinaceous infectious particles transmission also remains a concern, which can cause incurable neuro-degenerative disorders in humans known as transmissible spongiform encephalopathies. To prevent possible nosocomial infections which lead to about 22,000 death per year in the US and to about 25,000 death per year in Europe, the contrast medium dispensing system including the power syringes and filling & injecting set has to be entirely changed for each patient. The latter proves expensive and time consuming owing to the wasted contrast materials left over in the setup from each exam, the growing consumptions of disposable devices, and the prolonged pauses for replacing the entire setup with each patient.

In an effort to avoid cross-contamination between patients, many systems, such as, for example, disclosed in US 2004/0002685 A1 (Patzer), include a reusable set carrying the spike and a disposable set carrying the outlet luer connector providing the connection to the syringe, a pair of mating luer connectors for selectively joining the reusable and disposable set and a check valve downstream the spike. By switching the disposable set, one large container of contrast medium may be used with multiple patients.

DE 203 01 094 U1 (MEDTRON) discloses a disposable tubing system for a medicinal high-pressure injector for use with a contrast liquid, comprising a first and a second tubing part, wherein one end of the first tubing part (suction tube) is connected to a reservoir by means of a spike, and the opposite end is connected to the second tubing part (pressure tube), having a first end part connected to the suction tube and a second end part connected to a dosing device, such as an injection needle, wherein the suction tube preferably comprises a one-way valve, wherein the pressure tube preferably comprises a one-way valve, and wherein the pressure tube is further provided with a side entrance suitable for coupling with an injector. From the design of the disposable tubing system, it is obvious that a flow in the second tubing part from the patient towards the reservoir is excluded, opposite to the design according to the present invention, which does not contain a one-way valve in the second tubing part.

Furthermore, to verify whether a fluid dispensing unit, such as an injection needle, has been well inserted into a patients' vein, WO 2006/125789 A1 (Peters) discloses a disposable set for establishing a fluid connection between a fluid dispensing unit and a dosing device adapted to dispense the fluid into a patients' vein, the disposable set comprising a length of a tubing for establishing a fluid connection from the fluid dispensing unit towards and into the dosing device. The tubing comprises a first and a second tubing part, the first tubing part being provided to establish at a first end part a connection to a second end part of the second tubing part, and at a second end part a connection towards the fluid dispensing unit. The first tubing part comprises a one-way valve which is provided to permit a fluid flow from the fluid dispensing unit towards the dosing device and to prevent a backward fluid flow from the dosing device towards the fluid dispensing unit. The first end part of the first tubing part and the second end part of the second tubing part are in fluid connection with each other in a liquid tight manner by means of a releasable connection device. The releasable connection is adapted to permit a backflow from the patient into the second tubing part in the direction of the releasable connection device in the released position of the releasable connection and to prevent a backflow from the patient in the direction of the releasable connection device in the closed position of the releasable connection. Said device permits connecting the manifold or fluid reservoir of the fixed part of the fluid dispensing system to the dosing device for insertion into a patients' vein. Opening of the releasable connection between the first and second tubing part permits to verify whether or not the dosing device has been correctly inserted into the patients' vein by permitting a temporary backflow of blood into the dosing device. The risk of contamination of the fixed part of the fluid dispensing system is minimized by the presence of the one way valve. The latter system is commercially available under the trade name Transflux™ (P&R Medical, Diepenbeek, Belgium) and has commercially been used for many years.

Although the latter system is already a huge improvement over other commercial systems, in some situations, cross-contamination still remains a concern, for example when a patient is connected to said delivery system over an extended period of time.

DESCRIPTION OF THE INVENTION

It is therefore an object of the present invention to provide a device which permits connecting the manifold or fluid reservoir of the fixed part of the fluid dispensing system to the dosing device for insertion into a patients' vein, which permits to verify whether or not the dosing device has been correctly inserted into the patients' vein, and which permits to further minimize the risk to contamination of the fixed part of the fluid dispensing system, in particular preventing such contamination.

Surprisingly, this problem has been solved by the use of two or more consecutively arranged one-way valves in a tubing, permitting a one-way flow in the direction of a patient in said tubing suitable for the intravenous delivery of a fluid to a patient.

In particular, said problem has been solved with the disposable set according to the first claim, which is characterized by the inclusion of at least two consecutively arranged one-way valves in the first tubing part of the disposable set. The use of at least two consecutively arranged one-way valves in the first tubing part of the disposable set has not been disclosed nor suggested in WO 2006/125789 A1 or DE 203 01 094 U1, taken apart or together.

In particular, the tubing of the disposable set of this invention comprises a first and a second tubing part, the first tubing part being provided to establish at a first end part a connection to a second end part of the second tubing part and at a second end part a connection towards a fluid dispensing unit, the second tubing part being provided to establish at a first end part a connection towards a dosing device and at a second end part a connection to the first tubing part, wherein the first tubing part comprises a first one-way valve which is provided to permit a fluid flow from the dispensing unit towards the dosing device and to prevent a backward fluid flow from the dosing device towards the fluid dispensing unit, wherein the first end part of the first tubing part and the second end part of the second tubing part are in fluid connection with each other in a liquid tight manner by means of a releasable connection device, which releasable connection is adapted to permit a backflow (blood reflux control) from the patient into the dosing device and second tubing part in the direction of the releasable connection device in the released position of the releasable connection and to prevent a backflow (blood reflux) from the patient into the dosing device and second tubing part in the direction of the releasable connection device in the closed position of the releasable connection, characterized in that the first tubing part comprises one or more second one-way valves which are provided to permit a fluid flow from the second end of the first tubing part towards the first end of the first tubing part and to prevent a backward fluid flow from first end of the first tubing part towards the second end of the first tubing part. In practice this means that fluid is flowing from the second end part of the first tubing part towards the first end part of the second tubing part.

Preferably, the first tubing part comprises one second one-way valve.

The one or more second one-way valves provide the additional benefit that the contamination of the fixed part of the fluid dispensing system is nihil, as shown in the experimental part of this application.

Surprisingly, the inventor has found that a first tubing part comprising two or more, preferably two, valves reduces the contamination in the fixed part of the fluid dispensing system to an extent which is higher than the combined reduction power of the separate valves would suggest. In other words, when the first valve reduces the contamination due to the backward fluid flow flowing through the first valve, typically about 0.1 ml/hour, by $X_1$%, for example 1%, and the second valve reduces the contamination due to the backward fluid flow flowing through the second valve, typically about 0.1 ml/hour, by $X_2$%, for example 1%, then the contamination after the second valve in the direction of the dosing device is smaller than $X_1$ times $X_2$, for example 1%×1%=0.01%, and is virtually nihil. This synergetic effect was not observed in a single valve which contains, for example, two or more consecutive membranes. It further minimizes the risk of contamination of the fixed part of the fluid dispensing system, which is important, e.g. when the first one-way valve is faulty, when the procedure is not carried properly, or when the blood reflux is massive.

Preferably, the first and second tubing parts each only have two end parts, in casu have no side entrance, i.e. the only open ends are the first and second end parts, as defined in this application.

When in use, the second end part of the first tubing part of the disposable set of this invention may be coupled to the manifold, which is in turn connected to a fluid reservoir containing the contrast medium to be administered to the patient. The disposable set may however be coupled to any other fixed part of a fluid dispensing system. The opposite first end of the first tubing part is coupled to the second end part of the second tubing part. The second end part of the second tubing part is coupled to the first tubing part, the opposite first end of the second tubing is coupled to an injection needle or any other dosing device which is to be inserted in the patients' vein. A complete filling of both the tubing and the needle with fluid at the time the injection needle is inserted in the patients' vein must be ensured as delivering of air into the vein would expose the patient to high risk. As soon as the dosing device, in particular the injection needle has been inserted into the patients' vein and the connection with the reservoir has been established at the second end part of the first tubing, with the releasable connection between the first and second tubing part in the connected state, a fluid flow from the reservoir into the injection needle and the patients' vein is permitted.

By disconnecting the releasable connection device, the first tubing part is disconnected from the second tubing part, the first end part of the second tubing part is open to the air and permits to aspirate the injection needle, to permit a backflow of blood from the patients' vein into the second tubing part and to carry out the so-called reflux blood control which indicates that the dosing device or injection needle has been correctly inserted in the patients' vein. Once a reflux has been observed, the releasable connection device is brought into the connected state and blood reflux towards the manifold is inhibited by the presence of the first and second one-way valves and pressure from the first tubing part. The control that the dosing device or injection needle has been well inserted in the patients' vein is important as the risk to flowing of fluid from the reservoir into tissue surrounding the vein needs to be minimized as this may involve necrosis of surrounding tissue.

In other words, with the disposable set of this invention the second tubing part may be temporarily disconnected from the first tubing part to verify whether the dosing device has been correctly inserted into the patients' vein. Although the reflux control involves a backflow of blood from the patient into the tubing, the risk to contaminating the manifold is nihil as the two consecutively arranged one-way valves present in the first tubing part positioned between the releasable connection and the manifold, inhibit blood flow through the one-way valves and towards the fixed part. In particular, the first one-way valve reduces the risk of contamination of the fixed part of the fluid dispensing system a first time and the consecutively arranged one or more second one-way valves, arranged behind the first one-way valve in the direction of the fluid dispensing unit reduce the risk of contamination of the fixed part of the fluid dispensing system a second time.

Besides that, the risk to contamination is further reduced by ensuring that the part of the first tubing which extends between the first one-way valve and/or second one-way valve and the connection to the fixed part of the fluid dispensing system is sufficiently long.

According to a preferred embodiment of the invention, the releasable connection device comprises a first and a second connector part, the second connector part is fastened to a second end part of the second tubing part and the first connector part is mounted to an outlet side of the first one-way valve to permit a fluid flow from the fluid dispensing unit through the first one-way valve into the second tubing part when the first and second connector part have been engaged.

The risk of contamination towards the reservoir may be further reduced by having a second tubing part located at a position proximal to the patient with a relatively longer length as compared to the first tubing part.

Handling of, i.e. disconnecting and re-establishing the releasable connection is facilitated in case the first connector part is positioned on an end part of the first one-way valve on the side pointing towards the second tubing part.

The second one-way valve may be mounted at any position in the first tubing part, i.e. at any distance from the first and second connector part, respectively. However, to obtain the best results, each valve, in particular a first and second valve, should be mounted about 3 cm or more from each other. If the valves are mounted too close to each other the beneficial effect on the reduction of the contamination is decreased. Preferably, the second one-way valve is mounted at a distance about halfway the first tubing part, i.e. on about an equal distance from the first and second connector part, respectively.

The second one-way valve may be mounted either unreleasably or releasably attached to the tubing, using any combination of commonly known attachment means such as, for instance, glueing, pressing, clamping, or the use of any suitable connector known to the person skilled in the art, which permits to releasably connect two parts of a tubing, for example a luer connector or a bayonet coupling or any other coupling known to the person skilled in the art.

The first and second tubing part may also contain one or more clips (30) to temporarily close off the tubing part onto which the clip has been attached, such as by pressing or squeezing the elastic tubing together such that the inner flow is blocked. Advantageously, such clip (30) may be mounted in the second tubing part to close off the blood reflux, for example when the first and second tubing parts are disconnected. In this way, the patient's veins are not exposed to possible contaminants entering the open second end of the second tubing part. Advantageously, such clip (30) may be mounted in the first tubing part, between the second end (14) of the first tubing part (1) and the second one-way valve (24) to further reduce the risk of contamination.

The present invention also relates to a fluid dispensing system containing the above described disposable set.

The present invention also relates to the use of the above-described disposable set and fluid dispensing system for dispensing a fluid into a vein of a patient.

The present invention further relates to the use of the above-described disposable set and fluid dispensing system for dispensing a fluid to a patient.

The present invention also relates to a method for verifying blood backflow from a patient towards a fluid dispensing reservoir using the above-described disposable set and fluid dispensing system, according to which a second tubing part is connected to a dosing device which has previously been inserted into a patients' vein, the releasable connection is opened to permit a backflow from the patients' vein into the second tubing part and the releasable connection is re-established after the backflow of blood into the second tubing part has occurred and has been observed.

The invention is further elucidated in the attached figures and description of the figures.

Figures 1, 2:
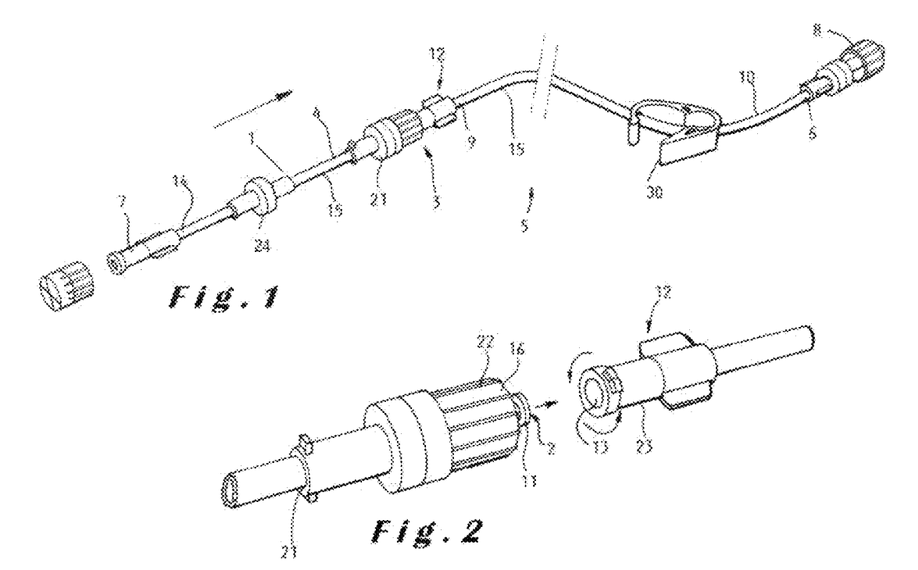
FIG. 1 shows a possible embodiment of the disposable set of the present invention.
FIG. 2 shows a detail of the first one-way valve integrated into the disposable set of the present invention.

As can be seen from FIG. 1, the disposable set 5 of the present invention comprises a tubing 15 with a first 1 and a second tubing part 10. The first tubing part 1 is located distal from the patient, the second tubing part 10 is located proximal to the patient. The first and second tubing part 1, 10 are in fluid connection with each other by means of a releasable connection device 11, 12. The first tubing part 1 comprises a first and a second end part 4, 14; the second tubing part 10 comprises a first and a second end part 6, 9. The first end part 4 of the first tubing part 1 is connected to the second end part 9 of the second tubing part 10 by means of the releasable connection device. The releasable connection device comprising a first connector part 22 which is mounted to the first end part 4 of the first tubing part 1, and a second connector part 23 which is mounted to the second end part 9 of the second tubing part 10.

The first tubing part contains a first one-way valve 3, which is provided to permit a fluid flow from the fluid dispensing unit 17, 18 towards the patient, or in other words from the second end part 14 towards the first end part 4 of the first tubing part 1. The first one-way valve 3 is provided to prohibit a fluid flow from the patient towards the fluid dispensing unit 17, 18, or in other words from the second end part 9 of the second tubing part 10 to the second end part 14 of the first tubing part 1. The first one-way valve 3 may be mounted somewhere centrally of the first tubing part 1, or shifted to one of the end parts. To facilitate manipulation, the first one-way valve is mounted in the proximity of the first end part 4 of the first tubing part 1, preferably at the end part.

Manipulation is further facilitated in that the first connector part 22 of the releasable connection 11 is mounted to an end part of the first one-way valve 3. The connector can be made of any suitable connector known to the person skilled in the art, which permits to releasably connect two parts of a tubing, for example a luer connector or a bayonet coupling or any other coupling known to the person skilled in the art.

The first tubing part further contains a second one-way valve 24, which is provided to permit a fluid flow from the fluid dispensing unit 17, 18 towards the patient, or in other words from the second end part 14 towards the first end part 4 of the first tubing part 1. The second one-way valve 24 is provided to prohibit a fluid flow from the patient towards the fluid dispensing unit 17, 18, or in other words from the second end part 9 of the second tubing part 10 to the second end part 14 of the first tubing part 1. The second one-way valve 24 may be mounted somewhere centrally of the first tubing part 1, or shifted from the middle to one of the end parts.

The second connector part 12 is mounted to a second end part 9 of the second tubing part 10. The first and second connector part 11, 12 are releasable connectible to each other in a liquid tight manner and permit a fluid flow from the fluid dispensing unit towards the patient, as well as the reverse. Usually, the second tubing part 10 proximal to the patient will have a relatively longer length as compared to the first tubing part 1, to prevent that any contamination ends up in the fixed part 17, 18, 20 of the fluid dispensing system. Anyhow, although contamination originating from a patient may end up in the releasable connecting device 11, 12 the two one-way valves 3, 24 will prevent further backflow towards the fluid dispensing unit 17, 18, forming the fixed part of the fluid dispensing system which is reusable with all patients. The risk for contamination of the fixed part may be further decreased by using a first tubing part 1 with a relatively long length. Within the scope of the present invention any type or combination of type of one-way valves considered suitable by the person skilled in the art may be used. Often, the use of a one-way valve made of a transparent material will be used as it assists in facilitating the control of the dispensing of the fluid.

A second end part 14 of the first tubing part 1 comprises a connector 7, for example a luer connector or any other suitable connector, for establishing a fluid connection towards the manifold or the fixed part of the fluid delivery device, that is reusable with every patient. In practice, the luer connector 7 will mostly be used to connect the dosing device to a manifold 20, which intervenes in dosing the contrast fluid contained in a reservoir 17 from that reservoir to the patient. The manifold 20 and reservoir 17 usually form part of the fixed part of the fluid delivery device.

A first end part 6 of the second tubing part 10 comprises a second connector, for example a luer connector 8 establishing the connection towards the dosing device with which the fluid is injected into the patients' vein. As a dosing device, any suitable device known to a person skilled in the art may be used. A suitable example of a dosing device is a syringe or injection needle.

Figure 3:
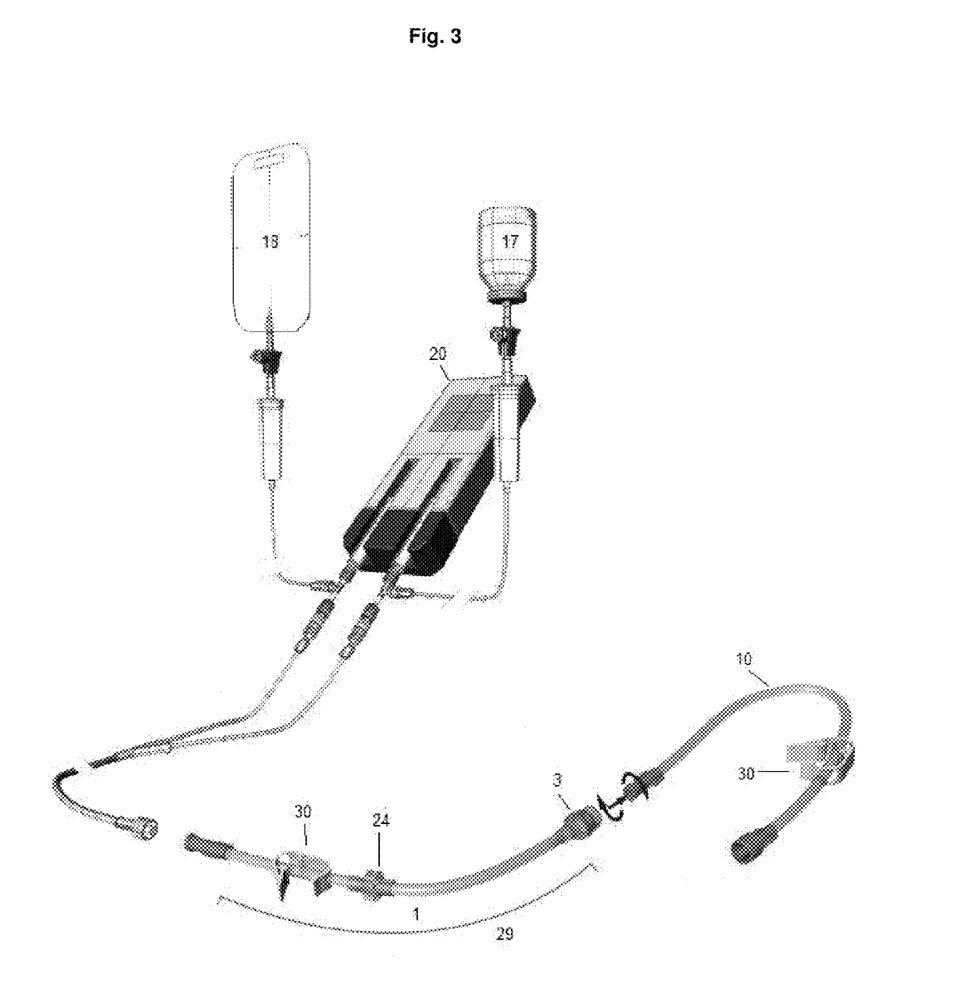
FIG. 3 shows the disposable set of the present invention integrated into a fluid dispensing system.

As can be seen in FIG. 3, the disposable set 5 of the present invention may be in direct connection with the fixed, reusable part 17, 18, 20 of the fluid dosing device or it may be indirectly connected to it, for example in case other instruments are present between the disposable set and the fixed part 17, 18, 20 of the system. In that case, the first tubing part 1 serves as a kind of safety area, as it increases the distance between the patient and the manifold and/or the fluid reservoir 17, 20 and the fixed part of the device 17, 18, 20 that is reusable with every patient and in that way assists in preventing contamination of the fixed part of the device. Although this is not necessary, additional lengths of tubing may be provided between the first tubing part 1 and the fixed part of the fluid dispensing system, using any connecting means considered suitable by the person skilled in the art.

The releasable connection 11, 12, used in the disposable set of this invention may be any connection known to the person skilled in the art, as long as it contains a first and a second part which are releasable connectible to each other and wherein the second part 12 in the disconnected state is open to the air to permit aspiration and a backflow of blood from a patients' vein into the second tubing part 10.

As is illustrated in FIG. 2, the first one-way valve comprises an inlet side 21 along which fluid from the fluid dispensing unit 17, 18 enters the first one-way valve, and an outlet side 2 on the opposite side of the first one-way valve, along which the fluid leaves the first one-way valve towards the patient. To facilitate manipulation of the releasable connection, the first connector part 22 is mounted to the outlet side 2 of the first one-way valve 3. The first connector part 22 preferably comprises a luer lock flange which is adapted to be received in a corresponding duct 13 of the second connector part 23 in a liquid tight manner. With a first connector part mounted to the outlet side 2 of the first one-way valve, any backflow from the second tubing part 10 towards the first connector part 22 is withheld by the first one-way valve.

Preferably, the first and second connector part 22, 23 are releasably connectible in a liquid tight manner by means of a threaded connection, provided on an outer wall of the duct 13 and an inner face of a circumferential wall 16 surrounding the flange over at least part of its length, as this provides a simple and quick opening and re-fastening. Thereby, the first flange 11 is adapted to be received in the corresponding second duct 13 in a liquid tight manner. However, any other releasable connecting means may be used, provided the liquid-tight connection is respected.

The second tubing part 10 may contain a clip 30 between the first end 6 and the second end 9 to temporarily close off the tubing part onto which the clip has been attached, such as by pressing or squeezing the elastic tubing together such that the inner flow is blocked. Furthermore, the first tubing part 1 may also contain a clip 30 between the second end 14 of the first tubing part 1 and the second one-way valve 24 to further reduce the risk of contamination.

The disposable system of the present invention is suitable for use with any fluid dispensing system for dispensing a fluid to a patient. The disposable system of this invention is particularly suitable for dispensing a fluid into veins, more particularly for dispensing contrast fluid into a patients' vein. However, the fluid dispensing system of this invention is suitable for dispensing any fluid to a patient and into a vein of a patient, for example the fluid dispensing system of this invention is suitable for use with pain pumps or dialysis devices. In that case, reflux control may be required from another organ of the patient, and may not involve blood but another fluid originating from the patient. The fluid dispensing system of this invention may also be used in a situation where a patient is moved from one fluid dispensing unit to another, as there is no risk to contamination of the first tubing part which each time is connected to fluid dispensing unit 17, 18. In that case the injection needle or dosing device remains inserted into the patients' vein, the second end part 14 of the first tubing is each time disconnected from a previous fluid dispensing system and re-connected to the next system. This is a big advantage as an injection needle has to be inserted only once and the disposable set can be taken along with the patient in case a plurality of successive tests and treatments need to be carried out. This is time saving and permits to at least double the number of CT scans that can be done on one day.

The tubing may be made of any suitable material known to the person skilled in the art. However, when used to dispense contrast fluid, preferably polyvinylchloride is used. Preferably, the tubing material is transparent as it allows the blood reflux to be observed visually. Preferably, the tubing material is flexible for easy coupling and decoupling. Preferably, the tubing material is suitable to be sterilized, as it is used in medical and/or sterile conditions.

The dimensions of the first and second tubing part are not critical to the present invention and may be adapted by the person skilled in the art to the intended application. In CT-scan systems, the distance and thus the length of the tubing between the injection needle and the reservoir containing the contrast medium will often be approximately 1 meter. Such tubing may, for example, have an internal volume of approximately 5-10 ml, the over-all content of the contrast fluid reservoir being approximately 110 ml. However, with MRI imaging, often the fluid is injected into the patients' vein under pressure and a somewhat larger distance needs to be bridged. To minimize the risk to local expansion of the tubing and to optimize the so-called bolus, usually use will be made of tubing having a relatively thicker material thickness. As in MR imaging, the contrast fluid volume is often limited to 10-15 ml, usually use will be made of a tubing having a smaller internal diameter and an internal volume of only approximately 3 ml, although this may be somewhat more or somewhat less. A commonly used length of tubing in MR imaging is approximately 120 cm, although this may be longer or shorter depending on the nature of the device used. However, the fluid dispensing system of this invention is not limited for use with contrast medium only, but is suitable for use with a wide variety of fluids that are to be delivered to a patient.

When in use, the first and second tubing part 1, 10 are used in the connected state of the connecting device 11, 12. The second tubing part 10 is connected to an injecting needle through the second luer connector 8. The first tubing part 1 is connected to the fluid dispensing system 20 through the first luer connector 7. After the connection has been established, the system is usually flushed with a physiologic fluid contained in reservoir 18. After the flushing has been terminated, the connection of the manifold 20 towards the reservoir 18 is closed, and the connection of the manifold towards the contrast fluid reservoir 17 is opened, so that contrast fluid may flow into the tubing 15. After having completely filled tubing 15 and the injection needle, the needle is inserted into the patients' vein. Reflux control, to verify whether the injection needle has been inserted in a correct manner into the patients' vein is done by disconnecting the first and second connector part 11, 12, aspirating the second tubing part 10 containing the injection needle and verifying whether or not there is a backflow of blood from the patient into second tubing part 10. After backflow into the second tubing part 10 has been observed, connection of the first and second connector part 11, 12 is re-established, blood back-flow into the second tubing part does no longer occur and flow of contrast fluid from reservoir 17 into the patients' vein may be permitted. Fluid is permitted to flow as indicated by the arrows in FIG. 1, from the reservoir into the first tubing part 1, through the second one-way valve 24, through the first one-way valve 3 and the second tubing part 10 into the injection needle and delivered in the patients' vein.

From the above, it will be clear that any contamination originating from the patient penetrates the second tubing part and could in principle reach the first one-way valve, after having passed the releasable connection. The first one-way valve will however nearly completely inhibit any further back-flow towards that fluid dispensing unit as it only permits a flow from the fluid dispensing unit to the patient. The second one-way valve will completely inhibit any further back-flow towards that fluid dispensing unit. It will be clear that the first tubing part between the first one-way valve and the fluid dispensing system functions as a kind of safety zone 29, and that the second one-way valve is additionally used to minimize the risk to contamination of the fluid dispensing system in case any contamination might end up in and past the first one-way valve. Thus, a system is provided, showing three measures of safety.

In particular, when use is made of a tubing with a small diameter, with the disposable set of the present invention flushing may be done with a diluted contrast medium which is a mixture of physiologic fluid and contrast medium as the reduced volume of the tubing permits to reduce losses of the contrast medium. This is preferred as otherwise the initial concentration of the contrast medium may be too low to give reproducible imaging.

Disconnecting the first and second part of the connecting device provides a reflux control by aspirating the dosing device and in that way permits to verify whether or not the injection needle has been inserted into the vein in a correct manner. In case the needle has been inserted into the patients' vein, a backflow of blood from the patient into the second tubing part 1 will be observed upon aspirating. In case the needle is not inserted in the vein, no backflow of blood will be observed and the needle has to be re-inserted. It is implicitly understood that the tubing material is sufficiently transparent for visual inspection of the backflow of blood.

The present invention also relates to a fluid dispensing system containing the above described disposable set.

The present invention further relates to a method for verifying a correct insertion of a dosing device into a patients' vein. This method comprises the steps of
1) connecting a second tubing part (10) to a dosing device which has previously been inserted into a patients' vein;
2) temporarily loosening or disengaging the releasable connection between the first and second connector part 11, 12 to permit a backflow of blood into the second tubing part;
3) establishing the blood backflow into the second tubing part; and
4) re-connecting the first and second connector part 11, 12 to permit a flow from the reservoir to the dosing device.

The invention will now be described in more detail by some examples without being limited thereto.

EXPERIMENTAL

To verify the safety of dual-valve disposable set and contrast fluid delivery system according to the invention and to justify its clinical use, an experiment was conducted in rabbits with intravenous injection of a diffusible radioactive compound $^{99m}$Tc-dimercaptopropionyl-human serum albumin ($^{99m}$Tc-DMP-HSA). It, once injected in a patient or animal, remains largely in the blood pool. The tracer was monitored by sampling the delivery system for checking if the radioactive compound (simulating infectious pathogens) from the patient line in tight contact with animal bloodstream is able to cross the safety zone (FIG. 3) and reach the dual-syringe injector system.

Materials and Methods

This animal study was approved by the institutional ethics and radioprotection committees. To simulate normal clinical scenario, the studies were performed using a power injector (Dual Shot GX; Nemoto Kyorindo, Tokyo, Japan) comprising two disposable syringes, one of 200 ml for contrast media infusion and the other of 100 ml for normal saline flushing, both coupled to each other and to a filling & injecting set through a T-connector. Twelve contrast medium dispensing systems according to the invention were tested according to the following two protocols:
a) Multiple uses of disposable syringes filled with saline solution (Protocol A) Both disposable syringes were filled with saline solution for further filling of several infusion sets (n=6).
b) Multiple uses of disposable syringes filled with contrast agent and saline solution in two separate power syringes (Protocol B), taking different viscosity into account.

For simulating normal clinical conditions, one syringe was loaded with Iomeron® 350 media (Iodinated contrast medium Iomeprol, Bracco, Konstanz, Germany) and the other one with saline solution. After filling with media in each delivery system, a volume of 100 ml of saline was pushed through the line (n=6).

The experiments were performed using normal white male New Zealand rabbits (n=2) weighing around 5.0 kg (Animal House, K. U. Leuven, Belgium). The animal was sedated by intramuscular administration of Ketalar (ketamine hydrochloride, Parke-Davis Warner-Lambert, Bornem, Belgium) and Ranpun (xylazine hydrochloride, Bayer A G, Leverkusen, Germany) at 0.5 ml/kg for both. Then, it was kept under sedation during the experiment using pentobarbital (Nembutal; Sanofi Sante Animale, Brussels, Belgium) intraperitoneally at 60 mg/kg. After fixation and restriction of the sedated rabbit in the supine position using a dedicated holder, a 22 G peripheral venous catheter (0.9 mm×25 mm, BD Insyte-W™, Madrid, Spain) was placed in the marginal vein of both ears. One of them was used for administration of the radiotracer solution and the other for connection of the patient-delivery system according to the invention to be tested and for blood withdrawal to control the remaining radioactivity in the animal over time.

A single dose of 370 MBq of $^{99m}$Tc-DMP-HAS was prepared as described in: Verbeke K A, Vanbilloen H P, de Roo M J, Verbruggen A M (1993) Technetium-99m mercaptoalbumin as a potential substitute or technetium-99m labeled red blood cells. Eur J Nucl Med 20: 473-482) and administered to the animal. Then, the infusion sets previously filled with saline solution or contrast medium along with saline solution was coupled to the contralateral catheter in such a way as to guarantee a contact between the solution and the animal blood without air in-between. Taking into account that an actual scan only takes a few minutes, the animal was left in connection with the patient line for 10 min. After that period, the patient line was carefully disconnected from the animal.

An aliquot of 10 ml as well as the whole content of 3.5 ml was collected by tapping from the opening end of the filling & injecting set (tube end 7, across the safety zone) and patient line (tube end 9), respectively. Their radioactivities were counted for 1 minute (cpm). Animal blood samples (□200 μL) were withdrawn for controlling the circulating activity during each test. Radioactivity measurements of the collected samples mounted in a sample changer (Wallac 1480 Wizard 3", Wallac, Turku, Finland) were done using a gamma counter (3-in. NaI(TI) well crystal) coupled to a multichannel analyzer.

Statistical analyses were carried out using GraphPad Prism V.3 software (GraphPad Software Inc., San Diego, Calif.). Numerical data of measured radioactivities were expressed as mean±standard deviation and compared between injector syringe set and natural background radiation using two-tailed Student's t test. A statistical significance was considered at a probability value smaller than 0.05.

Results

The rabbits tolerated well the experimental procedures including sedation, anesthesia, catheterization of marginal ear veins, tracer injection, and the multiple samplings over three hours per protocol, and recovered to normal status afterwards.

The patient delivery systems were tested according to two protocols: A) multiple uses of disposable syringes filled with saline solution, and B) multiple uses of the two disposable syringes one filled with contrast solution and the other one with saline solution. After connecting each patient line to a rabbit, which was i.v. injected with $^{99m}$Tc-DMP-HSA, samples collected from the filling & injecting set and patient line were counted for radioactivity in comparison with natural background.

The results obtained from saline and saline plus contrast protocols are shown in Table 1. For saline protocol, radioactivity detected in the blood circulation of the rabbit (1655903±593221 cpm per 0.2 ml blood) was statistically higher than that (52894±33080 cpm) in the patient line ($p<0.0001$). Actually there was no radioactivity detected from the filling & injecting set in comparison to the patient line across the safety zone (p=0.003). There were no significant differences between the radioactivity in the samples (8±3 cpm) from filling & injecting set and the natural background radiation (7±3 cpm) (p=0.726).

Likewise, in the contrast agent protocol, there were significant differences between the radioactivity detected in the blood circulation of the animal (1119107±183174 cpm per 0.2 ml blood) and the patient line (32991±20232); ($p<0.0001$). No radioactivity was found in any samples from the filling & injecting set (6±6 cpm) in great contrast to the patient line across the safety zone (p=0.003). Statistically there were no significant differences between samples from filling & injecting set (6±6 cpm) and natural background radiation (6±4 cpm); (p=0.955).

TABLE 1

Results of measurement of radioactivity in the samples from the experimental saline and contrast plus saline protocols as well as the blood of experimental animals using the filling & injecting set according to the invention.

|  |  | Animal blood (0.2 mL) CPM (n = 6) | Patient line CPM (n = 6) | Filling & injection set CPM (n = 6) | Natural background radiation CPM (n = 6) |
|---|---|---|---|---|---|
|  |  | Before Safety Zone |  | After Safety Zone |  |
| Saline protocol | Samples | 2,056,151 | 88,259 | 6 | 6 |
|  |  | 2,580,793 | 36,427 | 5 | 5 |
|  |  | 1,411,901 | 95,484 | 11 | 13 |
|  |  | 1,707,872 | 30,787 | 7 | 5 |
|  |  | 1,230,304 | 12,328 | 5 | 4 |
|  |  | 948,399 | 54,081 | 12 | 9 |

TABLE 1-continued

Results of measurement of radioactivity in the samples from the
experimental saline and contrast plus saline protocols as well as the blood of
experimental animals using the filling & injecting set according to the invention.

| | | Animal blood (0.2 mL) CPM (n = 6) Before Safety Zone | Patient line CPM (n = 6) | Filling & injection set CPM (n = 6) After Safety Zone | Natural background radiation CPM (n = 6) |
|---|---|---|---|---|---|
| | Mean | 1,655,903 | 52,894 | 8 | 7 |
| | SD | 593,221 | 33,080 | 3 | 3 |
| | p values | Filling & injecting set vs. Natural background radiation | | 0.726 | |
| | | Patient line vs. Natural background radiation | | 0.003 | |
| | | Animal blood vs. Natural background radiation | | <0.0001 | |
| | | Filling & injecting set vs. Patient line | | 0.003 | |
| | | Filling & injecting set vs. Animal blood | | <0.0001 | |
| | | Patient line vs. Animal blood | | <0.0001 | |
| Contrast protocol | Samples | 1,269,190 | 60,928 | 5 | 9 |
| | | 1,401,743 | 52,357 | 7 | 12 |
| | | 1,067,618 | 14,303 | 2 | 0 |
| | | 1,086,509 | 10,062 | 5 | 6 |
| | | 965,634 | 30,246 | 0 | 3 |
| | | 923,948 | 30,052 | 16 | 4 |
| | Mean | 1,119,107 | 32,991 | 6 | 6 |
| | SD | 183,174 | 20,232 | 6 | 4 |
| | p values | Filling & injecting set vs. Natural background radiation | | 0.955 | |
| | | Patient line vs. Natural background radiation | | 0.003 | |
| | | Animal blood vs. Natural background radiation | | <0.0001 | |
| | | Filling & injecting set vs. Patient line | | 0.003 | |
| | | Filling & injecting set vs. Animal blood | | <0.0001 | |
| | | Patient line vs. Animal blood | | <0.0001 | |

The invention claimed is:

1. A disposable set (5) for establishing a fluid connection between a fluid dispensing unit (17) and a dosing device adapted to dispense a fluid into a patient's vein, the disposable set comprising a length of a tubing (15) for establishing the fluid connection from the fluid dispensing unit towards and into the dosing device, wherein the tubing (15) comprises a first (1) and a second (10) tubing part, the first tubing part (1) being provided to establish at a first end part (4) a connection to a second end part (9) of the second tubing part (10), and at a second end part (14) a connection towards the fluid dispensing unit, the second tubing part (10) being provided to establish at a first end part (6) a connection towards the dosing device and the patient and at a second end part (9) a connection to the first tubing part (1), wherein the first tubing part (1) comprises a first one-way valve (3) which is provided to permit a fluid flow from the dispensing unit (17, 18) towards the dosing device and to prevent a backward fluid flow from the dosing device towards the fluid dispensing unit, wherein the first end part (4) of the first tubing part and the second end part (9) of the second tubing part (10) are in fluid connection with each other in a liquid tight manner by means of a releasable connection device (11, 12), of which a releasable connection is adapted to permit a backflow from the patient into the second tubing part (10) in a direction of the releasable connection device in a released position of the releasable connection and to prevent a backflow from the patient in the direction of the releasable connection device (11, 12) in a closed position of the releasable connection, characterized in that the first tubing part comprises one or more second one-way valves (24) which are provided to permit a fluid flow from the second end (14) of the first tubing part (1) towards the first end (4) of the first tubing part (1) and to prevent a backward fluid flow from the first end (4) of the first tubing part (1) towards the second end (14) of the first tubing part (1);

wherein the second end (14) of the first tubing part (1) comprises a connector (7) to connect the dosing device to a manifold (20), which intervenes in dosing the fluid contained in the fluid dispensing unit (17) and wherein said one or more second one-way valves (24) are arranged at a distance of 3 cm or more from the first one-way valve (3).

2. The disposable set as claimed in claim 1, characterized in that the disposable set comprises only one second one-way valve (24).

3. The disposable set as claimed in claim 1, characterized in that the releasable connection device comprises a first (11) and a second connector part (12), in that the second connector part (12) is fastened to a second end part (9) of the second tubing part (10) and in that the first connector part (11) is mounted to an outlet side (2) of the first one-way valve (3), to permit a fluid flow from the fluid dispensing unit through the first one-way valve (3) into the second tubing part (10) when the first (11) and second connector part (12) have been engaged.

4. The disposable set as claimed in claim 3, characterized in that the first connector part (11) is positioned on an end part of the first one-way valve (3) on a side oriented towards the second tubing part (10).

5. The disposable set as claimed in claim 1, characterized in that the one or more second one-way valve (24) is mounted on the first tubing part at a predetermined location between the first and the second end parts of the first tubing part, about an equal distance from the first and second end parts of the first tubing part, respectively.

6. The disposable set as claimed in claim 1, characterized in that the releasable connection device (11, 12) is a luer connector.

7. The disposable set as claimed in claim 1, characterized in that the first connector part (11) comprises a first luer lock flange which is adapted to be at least partly received within in a corresponding duct (13) of the second connector part (12) so as to form a liquid tight connection, to establish the fluid connection between the first and the second connector part.

8. The disposable set as claimed in claim 7, characterized in that the liquid tight connection of the first and second connector part (11, 12) is achieved by means of a bayonet coupling or a threaded connection on an outer wall of the duct (13) and an inner face of a circumferential wall (16) surrounding the first luer lock flange.

9. The disposable set as claimed in claim 1, characterized in that the second tubing part (10) has a length which is longer as compared to a length of the first tubing part (1).

10. The disposable set as claimed in claim 1, characterized in that the dosing device is an injection needle.

11. The disposable set as claimed in claim 1, characterized in that the first and/or second tubing part comprise one or more clips (30).

12. A fluid dispensing system containing the disposable set as claimed in claim 1.

13. A method for verifying blood backflow from a patient towards a fluid dispensing reservoir using the disposable set of claim 1, comprising the steps of:
  1) connecting the second tubing part (10) to a dosing device which has previously been inserted into a patient's vein;
  2) temporarily loosening or disengaging the releasable connection between the first and second connector part (11, 12) to permit a backflow of blood into the second tubing part;
  3) establishing the blood backflow into the second tubing part; and
  4) re-connecting the first and second connector part (11, 12) to permit a flow from the reservoir to the dosing device.

* * * * *

UNITED STATES PATENT AND TRADEMARK OFFICE
CERTIFICATE OF CORRECTION

PATENT NO. : 9,504,817 B2
APPLICATION NO. : 14/232777
DATED : November 29, 2016
INVENTOR(S) : Jean-Pierre Peters It is certified that error appears in the above-identified patent and that said Letters Patent is hereby corrected as shown below:

In the Specification

Column 10, Line 10:
Delete "1" and insert --10--.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*